United States Patent

Sheikh

[11] Patent Number: 5,966,815
[45] Date of Patent: Oct. 19, 1999

[54] WIRE CUTTER WITH FLUSH CUT AND HOLDING ABILITY

[75] Inventor: Hamid Sheikh, Santa Ana, Calif.

[73] Assignee: Ormco Corporation, Glendora, Calif.

[21] Appl. No.: 09/025,742

[22] Filed: Feb. 19, 1998

Related U.S. Application Data

[63] Continuation-in-part of application No. 08/990,044, Dec. 12, 1997, abandoned.

[51] Int. Cl.$^6$ ........................................................ B25F 3/00
[52] U.S. Cl. .................................. 30/124; 30/134; 30/135
[58] Field of Search ............................ 30/134, 135, 124; 433/4, 159, 160

[56] References Cited

U.S. PATENT DOCUMENTS

| | | |
|---|---|---|
| 144,837 | 11/1873 | Delano ........................................ 30/135 |
| 420,340 | 1/1890 | Ginther ....................................... 30/124 |
| 572,644 | 12/1896 | Lemm ......................................... 30/134 |
| 594,072 | 11/1897 | Forde .......................................... 30/134 |
| 778,140 | 12/1904 | Paff ............................................. 30/134 |
| 878,648 | 2/1908 | Low ............................................ 30/134 |
| 2,985,957 | 5/1961 | Freedman ................................... 30/124 |
| 3,777,398 | 12/1973 | Routh, Jr. .................................... 30/124 |
| 3,842,500 | 10/1974 | Cassel ......................................... 30/124 |
| 3,908,268 | 9/1975 | Brown ......................................... 30/124 |
| 3,922,781 | 12/1975 | Tippy .......................................... 30/124 |
| 4,326,334 | 4/1982 | Roux ........................................... 30/124 |
| 4,348,808 | 9/1982 | Nalbandyan ................................ 30/134 |
| 4,395,824 | 8/1983 | Puro ............................................ 30/134 |
| 4,404,746 | 9/1983 | Jansson et al. ............................. 30/124 |

FOREIGN PATENT DOCUMENTS

| | | | |
|---|---|---|---|
| 447389 | 12/1912 | France ........................................ 83/135 |
| 562095 | 5/1957 | Italy ............................................ 83/135 |
| 7926 | 3/1901 | United Kingdom ....................... 83/134 |

OTHER PUBLICATIONS

Ormco Corporation, *Ormco Orthodontic Products,* Product Manual, 1990 (8 pgs.).
Detronix Corporation, *Distal End Cutters,* Brochure, undated (p. 13).
Orthopli Corporation, *Cut & Holt Distal End Cutter (Flush Cut),* Brochure, undated (p. 10).

*Primary Examiner*—M. Rachuba
*Attorney, Agent, or Firm*—Wood, Herron & Evans, L.L.P.

[57] ABSTRACT

A distal end cutter having a flush cut and hold feature. The distal end cutter includes a pair of jaw members having respective cutting surfaces for cutting a wire, such as an archwire of an orthodontic appliance. Disposed adjacent to one of the cutting surfaces is a flat, resilient jaw portion which holds a cut off segment of the archwire. As the flat, resilient jaw portion may be disposed directly adjacent to the cutting surfaces during the wire cutting operation, very small wire segments may be cut and held by the device to prevent ejection of such wire segments into the mouth of a patient. In the preferred embodiment, the resilient jaw portion is a spring plate removably mounted to one of the jaw members.

16 Claims, 2 Drawing Sheets

WIRE CUTTER WITH FLUSH CUT AND HOLDING ABILITY

RELATED APPLICATION

This application is a continuation-in-part of U.S. Ser. No. 08/990,044, filed Dec. 12, 1997, now abandoned.

BACKGROUND OF THE INVENTION

The present invention generally relates to wire cutters and, more specifically, to those wire cutters having the ability to cut a wire flush to an adjacent surface or element and the ability to hold the cut off segment of wire.

Wire cutters are currently available in many different forms. Typically, wire cutters have a pair of pivotally connected, plier style handles connected to respective pairs of cutting jaws. The jaws have cutting surfaces which may comprise two sharp edges which either meet in abutting relationship or interact in a scissor-like fashion. If the cutting surfaces abut one another to cut a wire, one of the surfaces may simply be a flat anvil surface against which an opposing sharp cutting edge interacts to cut the wire.

In certain applications, such as in the orthodontic field, it is necessary not only to cut a section of wire, but also to hold the cut off segment to prevent that segment from ejecting or falling into the mouth of a patient. One orthodontic application in which this feature is desirable involves the distal end of an archwire in an orthodontic appliance. The archwire typically extends through a buccal tube at this location and a segment of wire may project outwardly from an end of the tube for various reasons. This segment of the archwire is ideally cut flush to the end of the buccal tube during installation of the appliance. Wire cutting may also be required during maintenance or adjustment procedures. In this regard, once an archwire has been attached to an orthodontic appliance in the mouth of a patient, various movements of the appliance often take place over time. During these movements, the archwire may "walk" or move through the brackets of the orthodontic appliance. This may cause the end of the archwire to again be exposed from the end of the buccal tube. The exposed wire segment may cause irritation to the surrounding mouth tissue of the patient. For this purpose, specifically designed wire cutters have developed, with some including a flush cut and/or holding ability. Wire cutters having a scissor-type action do not generally enable a flush cut to the buccal tube. Therefore, to enable a flush cutting and holding ability, wire cutters having a sharp edge on one jaw and an anvil on the other or those having various forms of abutting cutting edges have been the options of choice.

Certain orthodontic distal end cutters currently available include a cylindrical spring holding wire attached to a jaw having a sharp cutting edge. A clipped wire segment is meant to be held between the cylindrical spring holding wire and an opposing jaw after the wire is cut. This type of wire cutter may specifically be referred to as a distal end cutter having a flush cut and hold feature. The spring holding wire associated with these distal end cutters has certain significant disadvantages. First, because it is cylindrical in shape, the contact that the spring holding wire makes with the cut segment of the archwire is not directly adjacent to the cutting surface, but is displaced at least by the radius of the spring holding wire. Therefore, in the case of certain short segments of archwire extending from a buccal tube, for example, the cut off segment may not extend fully to the contact point of the spring wire. Since adequate contact may not be made between the spring holding wire and the archwire segment, the archwire segment may not be held firmly in place between the jaws. This archwire segment may therefore drop or eject into the mouth of the patient.

Moreover, spring holding wires have been connected to distal end cutters of the type that include a sharp cutting edge on one jaw and a flat anvil surface on the opposite jaw. In currently available devices, the spring holding wire has been connected adjacent to the sharp cutting edge such that it bears against the anvil surface during a cutting operation. As the jaws are moved together to cut an archwire, the spring holding wire moves laterally away from the cutting edge and generally along the axis of the archwire. Therefore, it may also move away from the end of the clipped archwire segment. This tends to lead to the same holding problems discussed above. Also, due to its circular cross section, a cylindrical spring holding wire will only make point contact with an archwire segment that also has a circular cross section. This may not supply enough gripping contact to keep the archwire segment from being ejected into a patient's mouth. Finally, distal end cutters, such as described above, have not had the ability to cut a relatively wide range of wire diameters, constructions and cross sections. Instead, users have to resort to a larger or smaller wire cutter.

For at least the reasons stated above, it would be desirable to provide a wire cutter, and more specifically an orthodontic distal end cutter, having the ability to cut very short segments of wire flush to the end of a buccal tube while also holding the clipped wire segment. It would also be desirable to provide such a wire cutter having the ability to cut a relatively wide range of wire diameters, constructions and cross sections.

SUMMARY OF THE INVENTION

The present invention therefore provides a wire cutter, which may specifically be designed for cutting and holding an orthodontic wire, such as an archwire. The wire cutter generally includes first and second operatively connected jaw members with respective cutting surfaces. For certain aspects of the invention, these cutting surfaces may be sharp edges interacting in various known manners to cut a wire. In the preferred embodiment, an abutting relationship exists between the cutting surfaces, as opposed to a scissor-like relationship. It is further preferred that one of the cutting surfaces is a flat anvil surface, while the opposing cutting surface is a sharp cutting edge interacting generally against the flat anvil surface. In accordance with the invention, a flat, resilient jaw portion is disposed on one of the jaw members adjacent a cutting surface thereof. During a cutting operation, a cut off segment of the wire is held between the flat, resilient jaw portion and the opposing jaw member.

In the preferred embodiment, the flat, resilient jaw portion is a rigid, spring biased plate connected to the jaw member which includes the anvil surface. In connection with this aspect of the invention, therefore, the cutting surface on this first jaw member is an anvil, while the cutting surface on the second jaw member is a sharp edge. The rigid, spring biased plate is connected adjacent the anvil with a lengthwise edge of the plate extending along a lengthwise edge of the anvil. The spring biased plate is preferably removable from the first jaw member, as by being connected thereto with a threaded fastening element. This may allow for repair or replacement of the plate and provides easy assembly. The wire cutter is preferably a distal end cutter and, therefore, the jaws include angled portions or generally L-shaped portions so that the wire cutter may be used in the mouth of a patient to easily reach the distal end of an archwire in a conventional manner.

The flat, resilient jaw portion provides better engagement with a clipped wire segment because its line of contact with the clipped wire segment may be disposed very close to the adjacent cutting surface. The line of contact also enables increased gripping of archwire segments compared to conventional cylindrically shaped spring holding wires. As an additional and separate advantage, the present invention provides a spring biased member on a jaw member having an anvil as opposed to a jaw having a sharp cutting edge. This, for example, can eliminate current problems associated with movement of the spring biased member away from the clipped wire segment. In a similar regard, the spring biased member is confined to move generally in a direction perpendicular to the longitudinal axis of the wire during a cutting operation. This further ensures the ability to clip small wire segments. The travel distance of the spring biased member may also be controlled to cut a relatively wide range of wire sizes.

These and other advantages and aspects of the invention will become more readily apparent to those of ordinary skill upon review of the following detail description of one preferred embodiment in conjunction with the accompanying drawings.

DETAILED DESCRIPTION OF THE PREFERRED EMBODIMENT

Figure 1:
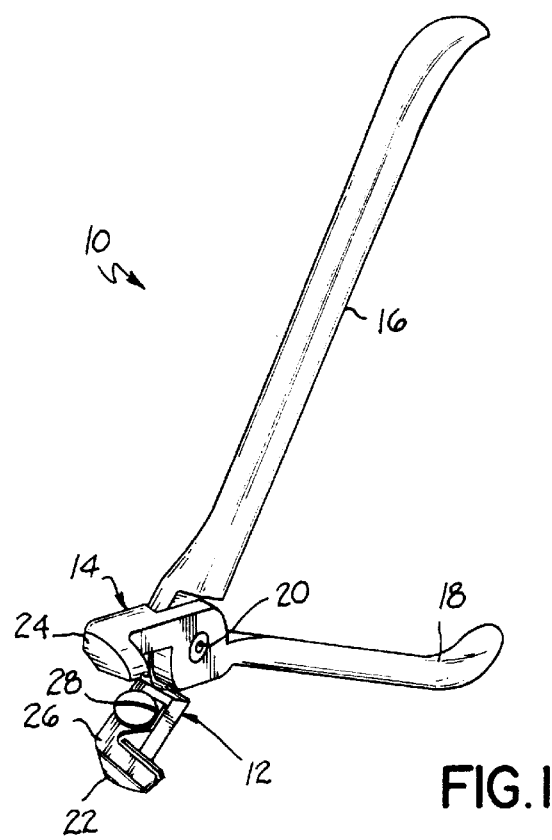
FIG. 1 is a perspective view of a distal end cutter constructed in accordance with the preferred embodiment.

A distal end cutter is shown in FIG. 1 constructed in accordance with the preferred embodiment of this invention. It will be understood that other types of wire cutters may also include the various features of this invention. The preferred wire cutter of this invention includes respective first and second jaw members 12, 14 each being connected to first and second plier type handles 16, 18. The first and second jaw members 12, 14 and first and second handles 16, 18 are joined at a pivot connection 20 in a conventional manner. In accordance with the preferred application of wire cutter as a distal end cutter, first and second jaw members 12, 14 include generally L-shaped or angled portions 22, 24. A flat, resilient jaw portion, in the preferred form of a rigid, spring biased plate 26 is removably connected to first jaw member 12 by a threaded fastener 28. It is contemplated that other types of flat, resilient jaw portions may be used to advantage as well. Plate 26 may also be further secured to jaw member 12 by a roll pin (not shown) inserted through plate 26 and into jaw member 12.

As shown in FIGS. 2, 4A–B and 5A–B, in the preferred form of wire cutter the cutting action is provided by respective cutting surfaces 30, 32 on first and second jaw members 12, 14. These cutting surfaces 30, 32 are contained on outer legs 22a, 24a of generally L-shaped portions 22, 24. As is conventional, cutting surfaces 30, 32 are disposed on an interior edge portion of each leg 22a, 24a for reasons that will become apparent. Preferably, cutting surface 30 is a flat anvil surface while cutting surface 32 is a sharp cutting edge. Cutting edge 32 interacts against flat anvil surface 30 to cut a wire segment 50. Spring biased plate 26 is shown just below flat anvil surface 30 in FIGS. 4A and 5A while resting in a non-gripping position. Preferably, distance "$d_1$" (FIG. 5A) between anvil surface 30 and upper surface 26a in this resting state is 0.015 inch. This enables cutting a relatively wide range of archwire sizes and shapes, for example, from 0.0155 inch round wire to 0.019 inch×0.025 inch rectangular wire. Plate 26 is also spaced from an upper surface 12a of jaw member 12 by a distance "$d_2$". Plate 26 moves downward, as shown in the figures, under a biasing force which may simply be provided by a slight upward positioning of plate 26 relative to surface 12a. The design of plate 26 or jaw member 12 may provide this gap. The distance of travel "$d_2$" for plate 26 is between about 0.010 inch to about 0.020 inch and, most preferably, is about 0.015 inch. Ideally, it is desirable to have spring 26 contact surface 12a, as shown in FIG. 5, before archwire 42 is either cut through or fractured by the action of edges 32, 34. The materials of construction for all elements used in constructing wire cutter are preferably surgical grade stainless steels or other alloys.

Figure 2:
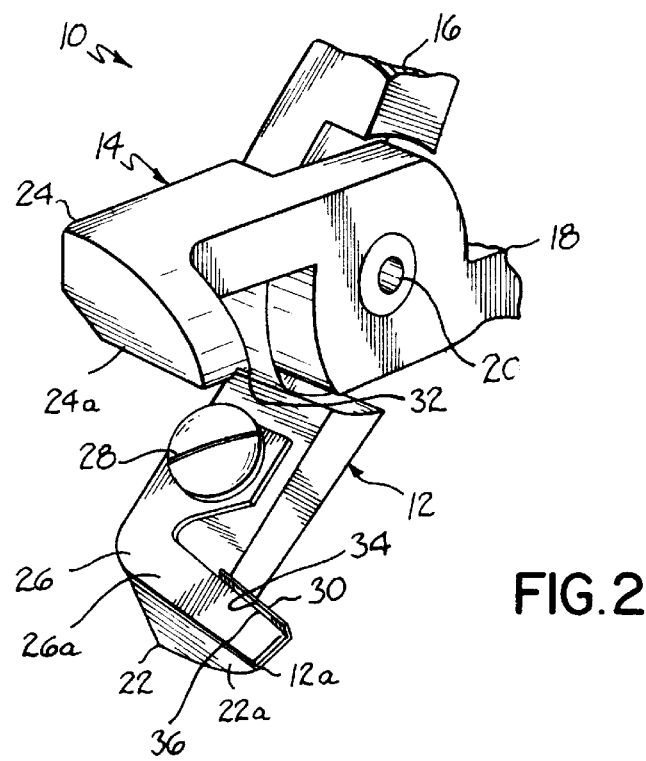
FIG. 2 is an enlarged perspective view of the first and second jaw members of the distal end cutter shown in FIG. 1.
Figure 5:
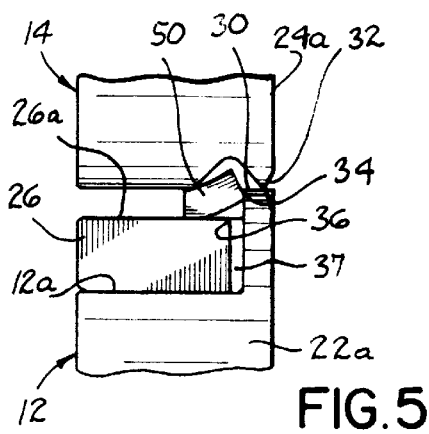
FIG. 5 is an enlarged front view of the jaw members taken generally along line 5—5 of FIG. 4B and showing the ability of the wire cutter to hold extremely short clipped wire segments.

As best shown in FIGS. 2 and 5, a lengthwise edge 34 of flat anvil surface 30 is disposed directly adjacent a parallel lengthwise edge 36 of spring biased plate 26. The distance between edges 34 and 36, that is, gap 37 shown in FIG. 5 is preferably about 0.020 inch. As will become more apparent from the description provided below, this allows flush cutting and holding of extremely short wire segments 50 protruding, for example, from a buccal tube in an orthodontic appliance.

Figure 5A:
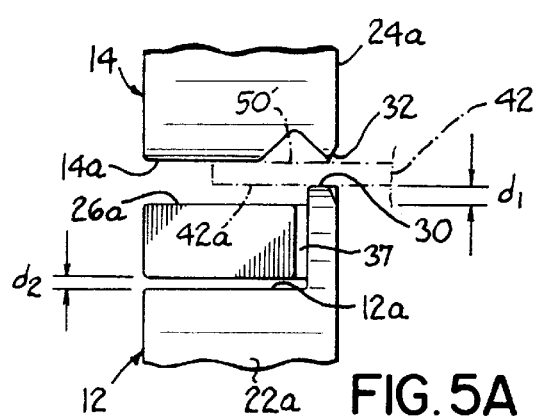
FIG. 5A is an enlarged front view similar to FIG. 5 but showing the wire cutter in a position just prior to clipping an archwire.

A review of FIG. 5A, for example, further illustrates another advantage of using a flat holding spring 26 as opposed to conventional cylindrical springs. Specifically, a flat holding spring 26 will provide line contact along a portion of the length of an archwire segment 50'. This line contact will occur along portion 42a of archwire 42. For purposes of better illustrating this advantage of the invention, wire segment 50' is longer than wire segment 50 shown in FIG. 5. Contrary to the invention, a cylindrical spring holding wire will contact a cylindrical archwire 42 at only a single point. For this reason, the flat holding spring will grip wire segments 50' better in many situations.

Figure 3:
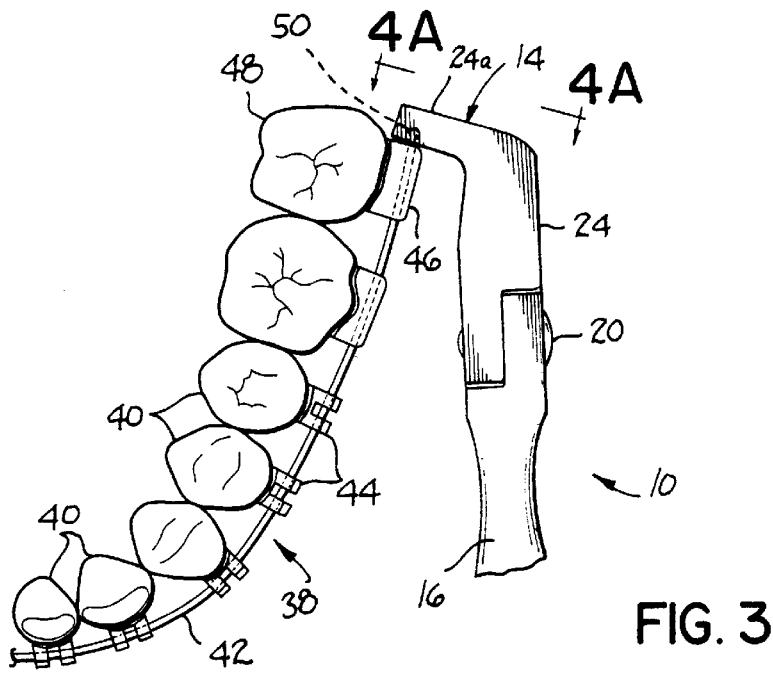
FIG. 3 is a top view of the preferred distal end cutter shown in use cutting a wire segment flush to a buccal tube in the mouth of a patient.

Referring now to FIG. 3, distal end cutter 10 is shown as it is used in a patient's mouth during procedures related to the implantation or maintenance of an orthodontic appliance 38. Orthodontic appliance 38 is shown connected to the lower or mandibular teeth 40 of a patient. In this regard, an archwire 42 may extend through various brackets 44 connected to teeth 40. A buccal tube 46 is typically attached to a rear molar 48. Generally, the archwire 42 may be chosen with such a length that a segment 50 protrudes from buccal tube 46. This segment 50 should be clipped flush to buccal tube 46 so as not to cause irritation to the patient.

Figure 4A:
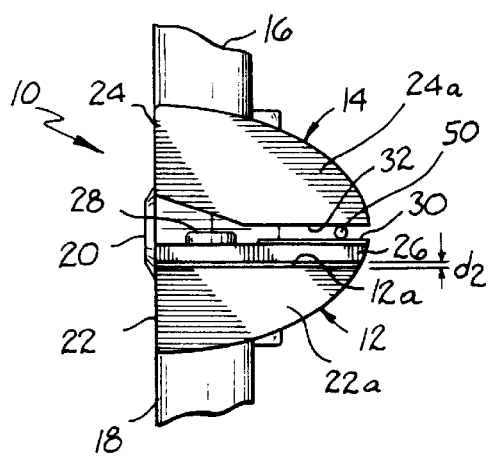
FIGS. 4A and 4B are end views showing a wire segment between the jaw members of the distal end cutter respectively before and after cutting the wire.
Figure 4B:
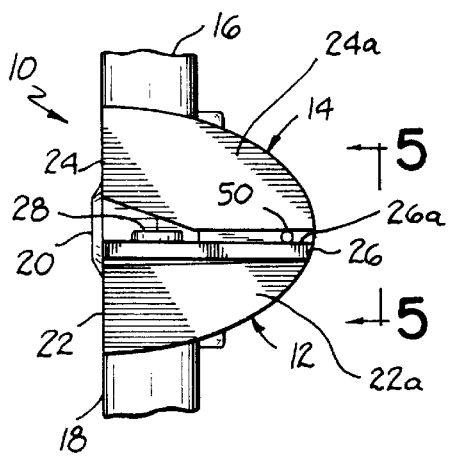

As further shown in FIG. 3, the conventional L-shape of each jaw member 12, 14 allows easy access to wire segment 50. For clarity purposes in FIG. 3, wire segment 50 is shown with a length that may be larger than the length experienced in many situations. Often, the length of segment 50 will be very short, such as on the order of about 0.030 inch. Even such short wire segments may cause irritation to the patient and therefore are desirably clipped flush to buccal tube 46. As shown progressively in FIGS. 4A and 4B, wire segment 50 is clipped by squeezing handles 16, 18 (FIG. 1) together to likewise move jaw members 12, 14 and cutting surfaces 30, 32 together (FIGS. 4B and 5). The clipped wire segment 50 is held between spring biased plate 26 and the opposing jaw member 14. As specifically shown in FIG. 5, extremely short wire segments may be cut and held in part because edge 36 of spring biased plate 26 is disposed directly adjacent to edge 34 of flat anvil surface 30 with a very slight gap 37.

The specific wire cutter disclosed herein is designed to cut archwires of various types and sizes ranging, for example, from 0.014 inch braided wire to 0.019 inch×0.025 inch rectangular wire. It will be appreciated that many modifications and substitutions of elements specifically described herein in connection with distal end cutter 10 may be made by those of ordinary skill in the art. These may, for example, include dimensional modifications made to accommodate different wire sizes, constructions or shapes. Such modifications falling within the spirit and scope of the present invention are intended to be covered and protected by any Letters Patent issuing from this application. Applicant therefore intends only to be bound by the legal scope of the appended claims.

What is claimed is:

1. A wire cutter for flush cutting and holding an orthodontic wire, the wire cutter comprising:

first and second operatively connected jaw members having respective side surfaces for abutting an orthodontic appliance and respective cutting surfaces for receiving a section of said orthodontic wire therebetween, at least one of said first and second jaw members being movable with respect to the other between an open position and a closed position, and one of the cutting surfaces being an anvil surface and another of the cutting surfaces being a sharp cutting edge which directly opposes and abuts the anvil surface adjacent the side surfaces when said jaws are in the closed position to thereby facilitate a flush cut of said orthodontic wire against said orthodontic appliance; and a flat, resilient jaw portion on said first jaw member and disposed adjacent the anvil surface and the sharp cutting edge such that, upon flush cutting the wire, an end segment thereof is held between the flat, resilient jaw portion and the second jaw member.

2. The wire cutter of claim 1 wherein the flat, resilient jaw portion is a rigid, spring biased plate connected to the first jaw member.

3. The wire cutter of claim 2 wherein the plate is removable from the first jaw member.

4. The wire cutter of claim 1 wherein the first and second jaw members include mating angled portions for flush cutting a distal end of said orthodontic wire adjacent a buccal tube of an orthodontic appliance.

5. The wire cutter of claim 4 wherein the first and second jaw members are pivotally connected together and respectively connected to first and second handles and the cutting surfaces are disposed on edges of the mating angled portions closer to the first and second handles.

6. The wire cutter of claim 1 wherein the flat, resilient jaw portion is a rigid, spring biased plate connected adjacent said anvil surface with a lengthwise edge of the spring biased plate extending along a lengthwise edge of said anvil surface.

7. The wire cutter of claim 6 wherein the spring biased plate has a wire gripping surface located below the anvil.

8. The wire cutter of claim 7 wherein the gripping surface is about 0.015 inch below the anvil.

9. A wire cutter for flush cutting and holding an orthodontic wire, the wire cutter comprising:

first and second operatively connected jaw members for receiving a segment of said orthodontic wire therebetween and having respective side surfaces for abutting an orthodontic appliance, at least one of said first and second jaw members being movable with respect to the other between open and closed positions;

an anvil surface disposed on said first jaw member;

a sharp cutting edge disposed on said second jaw member and disposed to directly oppose and abut said anvil surface adjacent the side surfaces when said jaws are in the closed position to cut the segment of orthodontic wire flush against the orthodontic appliance; and a flat, spring biased member connected to said first jaw member and extending along a lengthwise edge of said anvil surface for holding the cut segment of orthodontic wire.

10. The wire cutter of claim 9 wherein the spring biased member is a flat plate.

11. The wire cutter of claim 10 wherein the first and second jaw members are generally L-shaped and the plate is angled to follow the shape of the first jaw member.

12. The wire cutter of claim 11 further comprising first and second handles connected to the first and second jaw members, wherein the anvil surface and the cutting edge are disposed on edges of the jaw members closer to said handles.

13. The wire cutter of claim 11 wherein the plate is connected to the first jaw member in a replaceable manner.

14. The wire cutter of claim 13 wherein the plate is connected to the first jaw member by a threaded fastener.

15. The wire cutter of claim 10 wherein the spring biased plate is located below the anvil surface.

16. The wire cutter of claim 15 wherein the spring biased plate is located about 0.015 inch below the anvil.

* * * * *

UNITED STATES PATENT AND TRADEMARK OFFICE
CERTIFICATE OF CORRECTION

PATENT NO. : 5,966,815
DATED : October 19, 1999
INVENTOR(S) : Hamid Sheikh

It is certified that error appears in the above-identified patent and that said Letters Patent is hereby corrected as shown below:

Column 3,
Line 49, reads "cutter is" and should read -- cutter 10 is --.
Line 58, reads "cutter as" and should read -- cutter 10 as --.

Column 4,
Line 2, reads "cutter the" and should read -- cutter 10 the --.
Line 28, reads "cutter are" and should read -- cutter 10 are --.

Claim 16,
Line 2, reads "below the anvil." and should read -- below the anvil surface --.

Signed and Sealed this

Sixth Day of November, 2001

*Attest:*

*Attesting Officer*

NICHOLAS P. GODICI
*Acting Director of the United States Patent and Trademark Office*